US007758889B1

(12) United States Patent
Sagman et al.

(10) Patent No.: US 7,758,889 B1
(45) Date of Patent: Jul. 20, 2010

(54) FULLERENES IN TARGETED THERAPIES

(75) Inventors: Uri Sagman, Toronto (CA); Michael G. Rosenblum, Sugar Land, TX (US); Lon J. Wilson, Houston, TX (US)

(73) Assignee: Luna Innovations Incorporated, Roanoke, VA (US)

( * ) Notice: Subject to any disclaimer, the term of this patent is extended or adjusted under 35 U.S.C. 154(b) by 1461 days.

(21) Appl. No.: 10/623,110

(22) Filed: Jul. 18, 2003

Related U.S. Application Data

(60) Provisional application No. 60/398,325, filed on Jul. 24, 2002.

(51) Int. Cl.

| | |
|---|---|
| ***A01N 37/18*** | (2006.01) |
| ***A00N 55/02*** | (2006.01) |
| ***A61K 35/00*** | (2006.01) |
| ***A61K 31/44*** | (2006.01) |
| ***B01J 19/08*** | (2006.01) |

(52) U.S. Cl. .......................... 424/489; 514/2; 514/492; 514/680; 514/283

(58) Field of Classification Search ....................... None
See application file for complete search history.

(56) References Cited

U.S. PATENT DOCUMENTS 6,593,137 B1 * 7/2003 Erlanger et al. ............. 435/345
2002/0049495 A1 4/2002 Kutryk et al. .............. 623/1.47

FOREIGN PATENT DOCUMENTS

WO WO03/068185 8/2003

OTHER PUBLICATIONS

Laura L. Dugan et al. (carboxyfullerenes as neuroprotective agents), Proc. Natl. Acad. Sci. USA, vol. 94, pp. 9434-9439, Aug. 1997, Neurobiology.*
KL Tsai et al. (Mechanism of oxidative stress-induced intracellular acidosis in rat cerebellar astrocytes and C6 glioma cells), The Journal of PHysiology, vol. 502, Issue 1 161-174, Copyright 1997 by The Physiological Society.*
Williams JA, et al. (Targeting and therapy of human glioma xenografts in vivo using radiolabled antibodies), Int. J Radiat Oncol Biol Phys. Sep. 1990;19(3):633-42.*
CA Haberzettl, Nanomedicine: destination or Journey? Nanotechnology 13 (2002) R9-R13.*
Brettreich et al., *Angew. Chem. Int. Ed.* 39:1845-1848 (2000).
Holzinger et al., *Angew. Chem. Int. Ed.* 40:4002-4005 (2001).
Köhler et al., *Nature* 256:495-497 (1975).
Campbell, "Monoclonal Antibody Technology, The Production and Characterization of Rodent and Human Hybridomas," *Lab. Tech. in Biochem. & Mol. Biol.*, vol. 13 (1984).
Huse et al., *Science* 246:1275-1281 (1989).
Kantor et al., *Hybridoma* 1:473-482 (1982).
Morgan et al., *Hybridoma* 1:27-36 (1981).
Wilson et al., *Int. J. Cancer* 28:293-300 (1981).
Macey et al., *Am. J. of Physiologic Imaging* 3:1-6 (1988).
Koizumi et al., *Jpn. J. Cancer Res.* 79:973-981 (1988).
Williams et al., *Cancer Res.* 50:974s-979s (1990).
Rowlinson-Busza et al., *Current Opin. Oncol.* 4:1142-1148 (1992).
Wahl, *Cancer* 73:989-992 (1994).
Stirpe et al., *J. Biol. Chem.* 255:6947-6953 (1980).
Richardson et al., *Organic Letters* 2:1011-1014 (2000).
Camps et al., *J. Chem. Soc., Perkin Trans.* 1:1595-1596 (1997).

* cited by examiner

*Primary Examiner*—Michael G Hartley
*Assistant Examiner*—Nabila G Ebrahim
(74) *Attorney, Agent, or Firm*—Buchanan Ingersoll & Rooney PC

(57) ABSTRACT

Herein we disclose a composition, comprising a $C_n$-Ab, wherein $C_n$ is a fullerene or nanotube comprising n carbon atoms, and Ab is a moiety comprising an antigen-binding site and is linked to the Cn. The composition can further comprise a therapeutic molecule associated with the $C_n$-Ab. Also, we disclose a method of treating a disease in a mammal, comprising administering to the mammal an effective amount of the composition.

16 Claims, 13 Drawing Sheets

Taxol is Our First Drug

Drug =

Taxol

Synthesis of the Protected Thioldiamide Malonate Derivative of Fullerene

70

80

80

90

100

1 2 3

3

4

5

6 7 8

8

9

9

4

FULLERENES IN TARGETED THERAPIES

The present application claims priority from Ser. No. 60/398,325, filed Jul. 24, 2002.

BACKGROUND OF THE INVENTION

1. Field of the Invention

The present invention relates generally to the field of targeted therapies. More particularly, it concerns compositions comprising fullerenes or nanotubes associated with antibodies or targeting peptides, and optionally further associated with therapeutic molecules.

2. Description of Related Art

In general, "targeted therapies" are therapeutic compositions and methods that involve the delivery of a drug to a particular diseased cell, tissue, organ, or organ system in a mammal, such as a human or a mammal providing esthetic, economic, or research benefits to humans. The benefits of a targeted therapy include the potential to use less of the drug and the minimizing of systemic side effects the drug may have on the mammal.

Antibodies, including monoclonal antibodies, and targeting peptides are known which engage in highly specific physical interactions with particular antigens.

Linking a therapeutic molecule directly to an antibody or targeting peptide has been attempted, but has encountered a number of difficulties. Frequently, the antibody or targeting peptide has multiple sites at which reaction with the therapeutic molecule can occur, and vice versa, and reaction at some of those sites can lead to changes in the drug's or the antibody or targeting peptide's structure and potentially impair its function. Also, if the therapeutic molecule's and the antibody or targeting peptide's active sites are free to move relative to each other (while remaining linked), the therapeutic molecule and the antibody or targeting peptide may interact physically or chemically (through favorable van der Waals interactions, hydrophobic interactions, hydrogen bonding, or ionic association, among others) and adopt conformations that change the structure and potentially impair the functions of the drug, the antibody or targeting peptide, or both.

Therefore, a need exists for improved compositions for use in targeted therapies.

Fullerenes, of which the best known example is $C_{60}$, were first reported by Kroto et al., *Nature* (1985) 318:162. Since then, the ready derivatization of fullerenes has allowed a wide variety of derivatized fullerenes to be prepared and their properties explored.

Amphiphilic derivatized fullerenes have been reported by Hirsch et al., *Angew. Chem. Int. Ed* (2000) 39(10):1845-1848. The derivatized fullerenes of Hirsch comprised one dendrimeric group comprising 18 carboxylic acid moieties and five hydrophobic moieties each comprising a pair of lipophilic $C_{12}$ hydrocarbon chains. Freeze-fracture electron micrography of aqueous solutions of the amphiphilic derivatized fullerenes revealed that the amphiphilic derivatized fullerenes formed bilayer vesicles (by which is meant, a vesicle defined by a membrane comprising an external layer of amphiphilic derivatized fullerene molecules substantially all oriented with their hydrophilic groups to the exterior of the vesicle, and an internal layer of amphiphilic derivatized fullerene molecules substantially all oriented with their hydrophilic groups to the interior of the vesicle, wherein the hydrophobic groups of the molecules of the external layer are in close proximity to the hydrophobic groups of the molecules of the internal layer) with diameters from about 100 nm to about 400 nm.

Carbon nanotubes and methods for their derivatization are known. Holzinger et al., *Angew. Chem. Int. Ed.* (2001) 40(21):4002-4005 report the cycloaddition of nitrenes, the addition of nucleophilic carbenes, and the addition of radicals, to the sidewalls of carbon nanotubes.

SUMMARY OF THE INVENTION

In one embodiment, the present invention relates to a composition comprising a $C_n$-Ab, wherein $C_n$ is a fullerene or nanotube comprising n carbon atoms, and Ab is a moiety comprising an antigen-binding site and is linked to the $C_n$. The composition can further comprise a therapeutic molecule associated with the $C_n$.

In another embodiment, the present invention relates to a method of treating a disease in a mammal, comprising administering to the mammal an effective amount of a composition comprising (i) a $C_n$-Ab, wherein $C_n$ is a fullerene or nanotube comprising n carbon atoms, and Ab is a moiety comprising an antigen-binding site and is linked to the $C_n$ and (ii) a pharmaceutically-acceptable carrier.

In certain embodiments, the composition provides a fullerene or nanotube core which allows precise localization of linking reactions and provides a fixed structure which minimizes the freedom of movement of the Ab and a therapeutic molecule relative to each other, thus minimizing the drawbacks discussed above.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
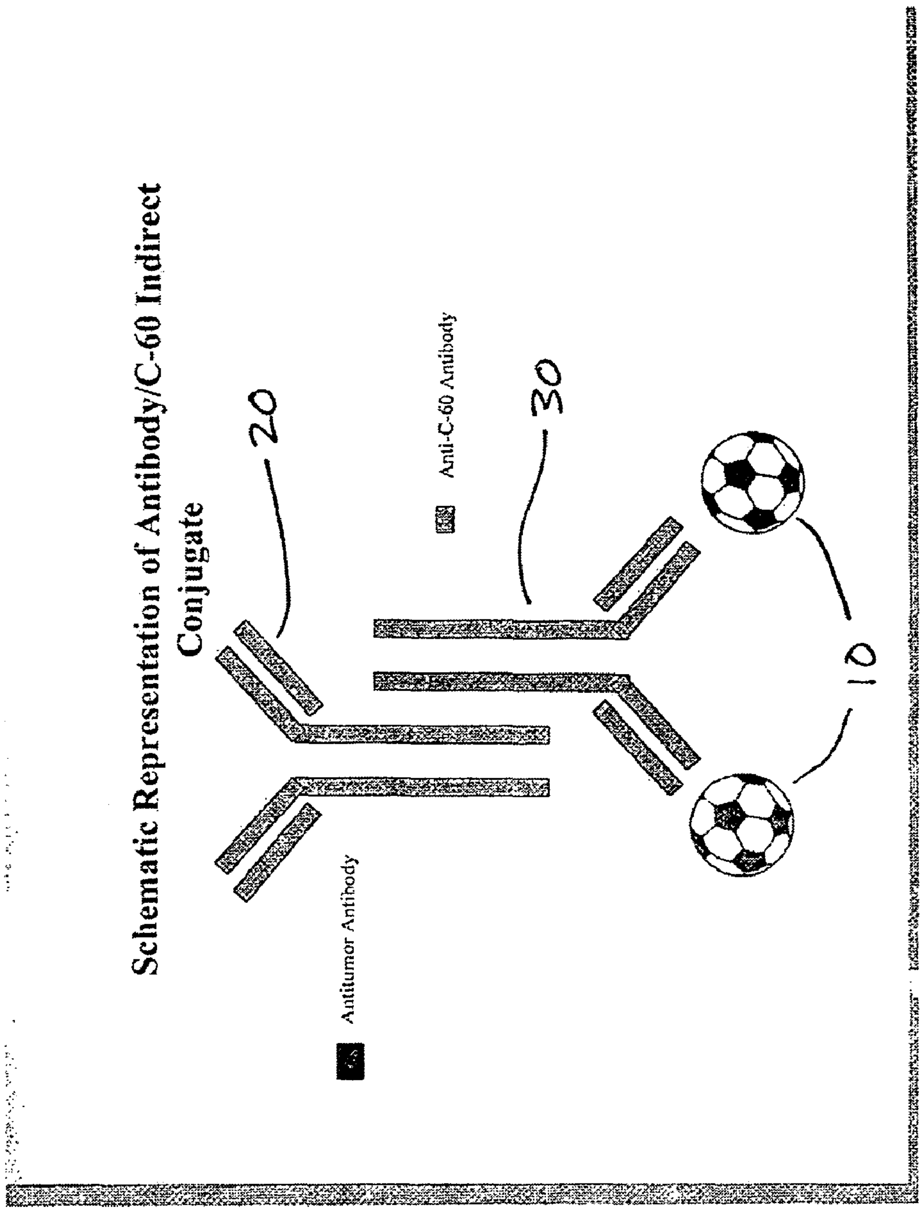
FIG. 1 shows a schematic representation of a $C_n$-Ab conjugate associated by a noncovalent antibody-mediated interaction.

In one embodiment, the present invention relates to a composition, comprising:

a $C_n$-Ab, wherein $C_n$ is a fullerene or nanotube comprising n carbon atoms, and Ab is a moiety comprising an antigen-binding site and is linked to the $C_n$.

$C_n$ refers to a fullerene moiety comprising n carbon atoms or a nanotube moiety comprising at least n carbon atoms. Buckminsterfullerenes, also known as fullerenes or, more colloquially, buckyballs, are closed-cage molecules consisting essentially of $sp^2$-hybridized carbons. Fullerenes are the third form of pure carbon, in addition to diamond and graphite. Typically, fullerenes are arranged in hexagons, pentagons, or both. Most known fullerenes have 12 pentagons and varying numbers of hexagons depending on the size of the molecule. Common fullerenes include $C_{60}$ and $C_{70}$ (i.e., n=60 or n=70), although fullerenes comprising up to about 400 carbon atoms are also known.

Single-wall carbon nanotubes, also known as single wall tubular fullerenes, are cylindrical molecules consisting essentially of $sp^2$-hybridized carbons. In defining the size and conformation of single-wall carbon nanotubes, the system of nomenclature described by Dresselhaus et al., *Science of Fullerenes and Carbon Nanotubes*, Ch. 19, ibid. will be used. Single wall tubular fullerenes are distinguished from each other by a double index (x, y), where x and y are integers that describe how to cut a single strip of hexagonal graphite such that its edges join seamlessly when the strip is wrapped onto the surface of a cylinder. When x=y, the resultant tube is said to be of the "arm-chair" or (x, x) type, since when the tube is cut perpendicularly to the tube axis, only the sides of the hexagons are exposed and their pattern around the periphery of the tube edge resembles the arm and seat of an arm chair repeated n times. When y=0, the resultant tube is said to be of the "zig zag" or (x, 0) type, since when the tube is cut perpendicular to the tube axis, the edge is a zig zag pattern. Where $x \neq y$ and $y \neq 0$, the resulting tube has chirality. The electronic properties of the nanotube are dependent on the conformation, for example, arm-chair tubes are metallic and have extremely high electrical conductivity. Other tube types are metallic, semi-metals or semi-conductors, depending on their conformation. Regardless of tube type, all single-wall nanotubes have extremely high thermal conductivity and tensile strength.

The single wall carbon nanotube can be a cylinder with two open ends, a cylinder with one closed end, or a cylinder with two closed ends. Generally, an end of a single wall carbon nanotube cylinder can be closed by a hemifullerene, e.g., a (10, 10) carbon nanotube can be closed by a 30-carbon hemifullerene. If the single wall carbon nanotube has one or two open ends, the open ends can have any valences unfilled by carbon-carbon bonds within the single wall carbon nanotube filled by bonds with hydrogen, hydroxyl groups, carboxy groups, or other groups. In one embodiment, the unfilled valences are filled by bonds with —COOH, or a salt or ester thereof.

In one embodiment, the $C_n$ can be a fragment of a fullerene or a fragment of a single wall carbon nanotube. A fragment of a single wall carbon nanotube can be generated by fluorination and subsequent pyrolysis, and a fragment of a desired size can be isolated by size separation by any appropriate technique, such as size-exclusion chromatography, nanopore filtration, capillary electrophoresis, or centrifugation, among others. In one embodiment, the fragment of a single wall carbon nanotube is about 20 nm in length.

In another embodiment, the $C_n$ is not a fragment of a fullerene or a fragment of a single wall carbon nanotube.

The value of n can be other than a value explicitly stated herein and remain within the scope of the present invention.

The $C_n$ can be substituted or unsubstituted. By "substituted" is meant that a group of one or more atoms is covalently linked to one or more atoms of the $C_n$. Exemplary groups include, but are not limited to, malonate groups and groups derived from malonate, among others. In one embodiment, the $C_n$ is substituted with one or more water-solubilizing groups. Water-solubilizing groups are polar groups (that is, groups having a net dipole moment) that render the generally hydrophobic fullerene core soluble in water.

A powerful observation regarding fullerenes and nanotubes is that they generally allow for precise localization of substituent molecules during the addition of substituents thereto.

Ab refers to a moiety comprising an antigen-binding site. An "antigen," as used herein, is a chemical compound or a portion of a chemical compound which can be recognized by a specific chemical reaction, a specific physical reaction, or both with another molecule. The antigen-recognition site of an antibody is an exemplary, but non-limiting, antigen-binding site. Examples of moieties comprising antigen-binding sites include, but are not limited to, monoclonal antibodies, polyclonal antibodies, Fab fragments of monoclonal antibodies, Fab fragments of polyclonal antibodies, $Fab_2$ fragments of monoclonal antibodies, and $Fab_2$ fragments of polyclonal antibodies, among others. Single chain or multiple chain antigen-recognition sites can be used. Multiple chain antigen-recognition sites can be fused, joined by a linker, or unfused and unlinked.

The Ab can be selected from any known class of antibodies. Known classes of antibodies include, but are not necessarily limited to, IgG, IgM, IgA, IgD, and IgE. The various classes also can have subclasses. For example, known subclasses of the IgG class include, but are not necessarily limited to, IgG1, IgG2, IgG3, and IgG4. Other classes have subclasses that are routinely known by one of ordinary skill in the art.

The Ab can be derived from any species. "Derived from," in this context, can mean either prepared and extracted in vivo from an individual member of a species, or prepared by known biotechnological techniques from a nucleic acid molecule encoding, in whole or part, an antibody peptide comprising invariant regions which are substantially identical to antibodies prepared in vivo from an individual member of the species or an antibody peptide recognized by antisera specifically raised against antibodies from the species. Exemplary species include, but are not limited to, human, chimpanzee, baboon, other primate, mouse, rat, goat, sheep, and rabbit, among others known in the art. In one embodiment, the Ab is chimeric, i.e., comprises a plurality of portions, wherein each portion is derived from a different species. A chimeric antibody, wherein one of the portions is derived from human, can be considered a humanized antibody.

Abs are available that recognize antigens associated with a wide variety of cell types, tissues, and organs, and a wide variety of medical conditions, in a wide variety of mammalian species. Exemplary medical conditions include, but are not limited to, cancers, such as lung cancer, oral cancer, skin cancer, stomach cancer, colon cancer, nervous system cancer, leukemia, breast cancer, cervical cancer, prostate cancer, and testicular cancer; arthritis; infections, such as bacterial, viral, fungal, or other microbial infections; and disorders of the skin, the eye, the vascular system, or other cell types, tissues, or organs; among others.

Exemplary Abs include, but are not limited to, those derived from antibodies against vascular endothelial growth factor receptor (VEGF-r) (available from Imclone, New York, N.Y.), antibodies against epidermal growth factor receptor (EGF-r) (available from Abgenix, Fremont, Calif.), antibodies against polypeptides associated with lung cancers (available from Corixa Corporation, Seattle, Wash.), and antibodies against human tumor necrosis factor alpha (hTNF-α) (available from BASF A.G., Ludwigshafen, Germany), among others known in the art.

Abs can be prepared by various techniques known in the art. These techniques include, but are not limited to, the immunological technique described by Kohler and Milstein in Nature 256, 495-497 (1975) and Campbell in "Monoclonal Antibody Technology, The Production and Characterization of Rodent and Human Hybridomas" in Burdon et al., Eds., Laboratory Techniques in Biochemistry and Molecular Biology, Volume 13, Elsevier Science Publishers, Amsterdam (1985); as well as by the recombinant DNA techniques described by Huse et al in Science 246, 1275-1281 (1989); among other techniques known to one of ordinary skill in the art.

In one embodiment, the Ab is derived from murine ZME-018, which recognizes the gp240 antigen present on more than 80% of melanoma biopsies and cell lines. The gp240 antigen can also be recognized by Abs derived from SCFVMEL, an SCFV antibody; dSCFVMEL, a diabody antibody; and GD2, a chimeric antibody. In another embodiment, the Ab is derived from HuM195, a humanized antibody which recognizes CD-33, an antigen present on AML and CML cells in the hematopoeic system. In a different embodiment, the Ab is derived from herceptin, a chimeric antibody which recognizes the HER2 antigen associated with certain breast, colon, and lung tumors. The HER2 antigen can also be recognized by Abs derived from the BACH 250 chimeric antibody, the ML 3-9 SCFV antibody, or the C 6.5 diabody antibody. In another embodiment, the Ab is derived from αMMP9, a chimeric antibody which recognizes the MMP9 antigen associated with certain lung tumors. In a different embodiment, the Ab is derived from Campath 1H, an antibody which recognizes the CD-52 antigen associated with leukemias. In a further embodiment, the Ab is derived from anti-TNF-R1, an antibody which recognizes the TNF-R1 antigen associated with leukemias. In yet a different embodiment, the Ab is derived from anti-CD-38, an antibody which recognizes the CD-38 antigen associated with leukemias. In still a further embodiment, the Ab is derived from Bexxar, an antibody which recognizes the CD-20 antigen associated with leukemias. In still an additional embodiment, the Ab is derived from VEGF121 or SuperGen, antibodies which recognize the VEGF Receptor 2 antigen associated with solid tumors.

In addition to the listed antibodies, the Ab can be constructed to recognize a target antigen associated with a solid tumor. For example, the Ab can be constructed to recognize HER2/neu, MUC-1, HMFG1, or EGFr, associated with breast tumors; MMP-9, HER2/neu, or NCAM, associated with lung tumors; HER2 or 171A, associated with colon tumors; gp240, gangliosides, or integrins, associated with melanomas; HER2 or CA-125, associated with ovarian tumors; or EGFr or tenascin, associated with brain tumors. This list of target antigens and tumor types is exemplary and not limiting.

Figure 2:
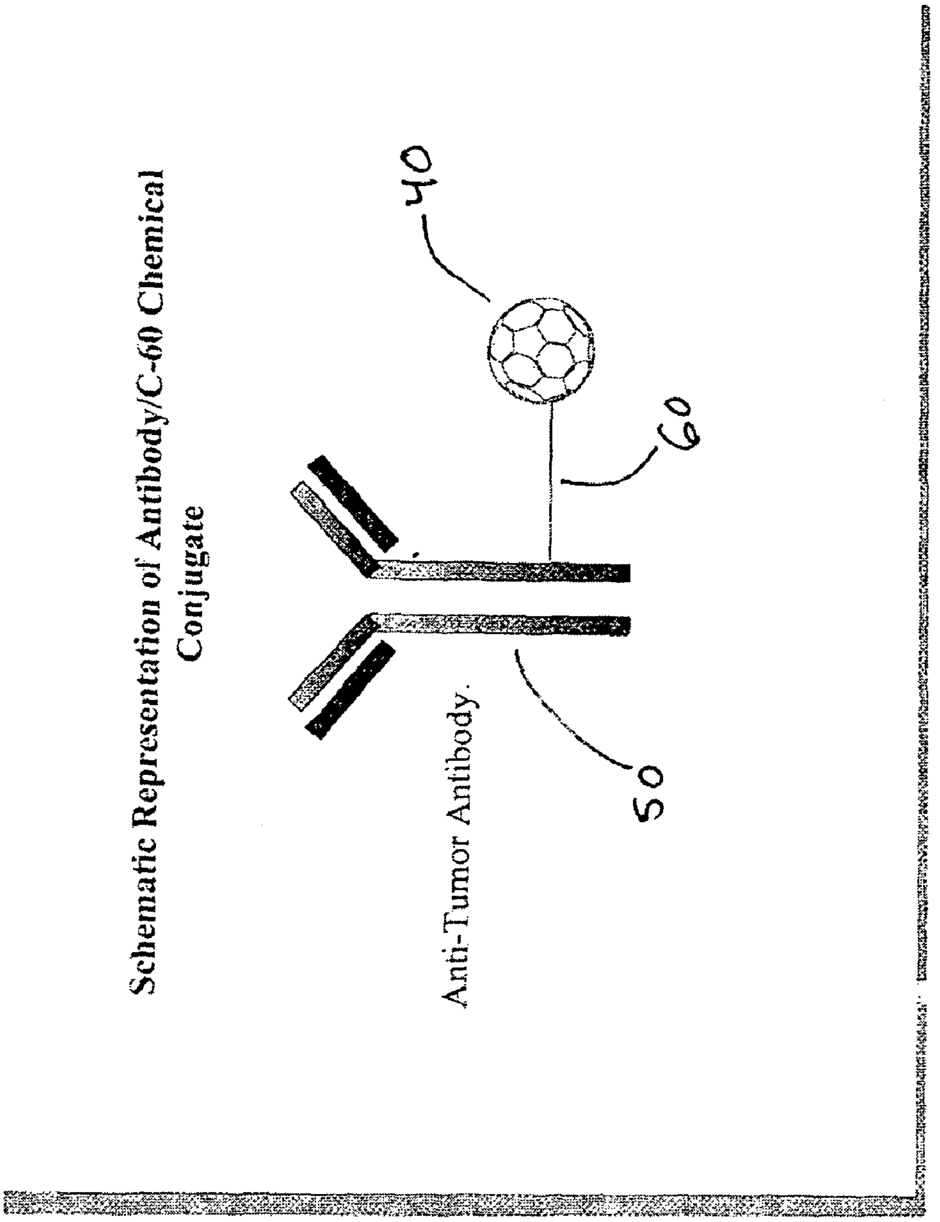
FIG. 2 shows a schematic representation of a $C_n$-Ab conjugate associated by a covalent linker.
Figure 3:
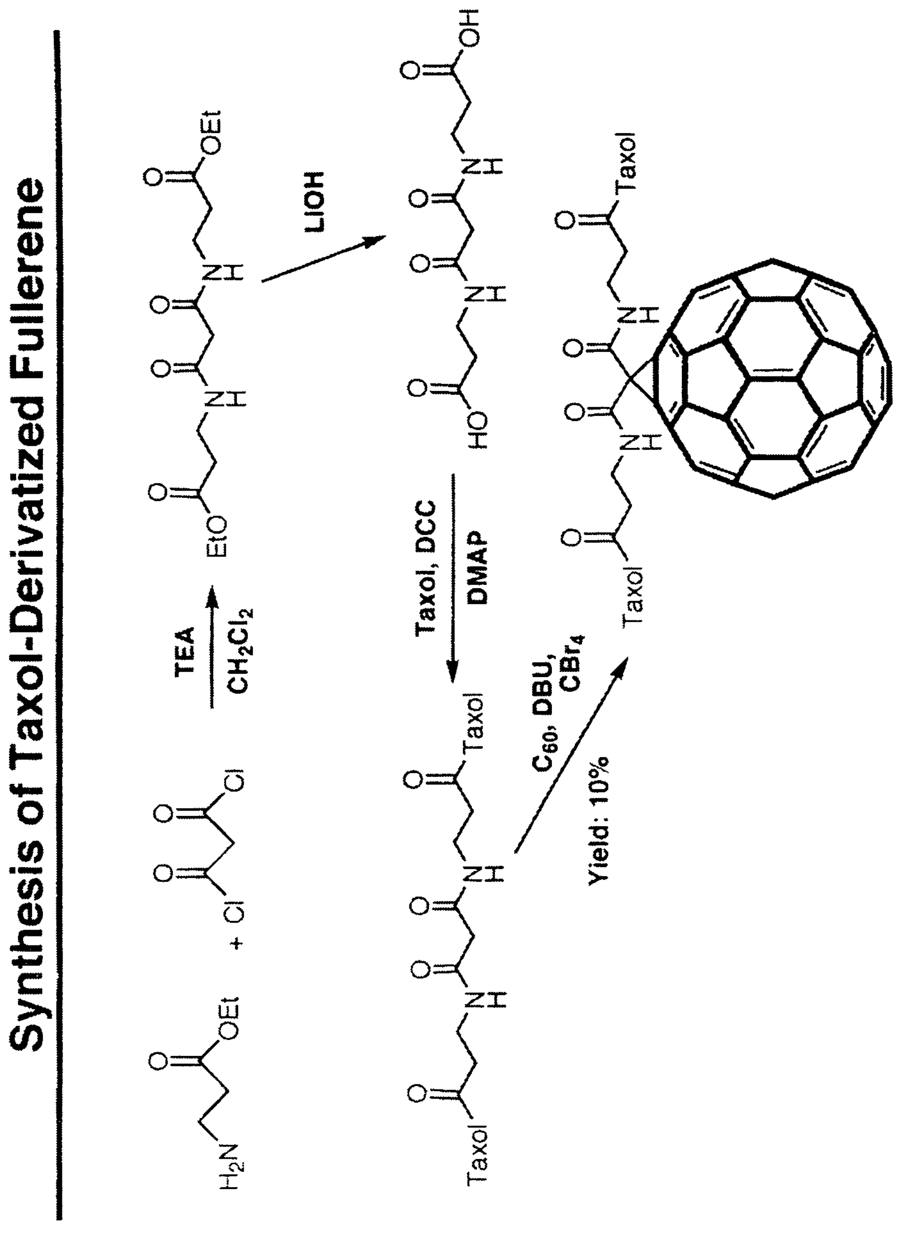
FIG. 3 shows a synthesis scheme for the production of a fullerene core covalently linked to the drug Taxol.
Figure 4:
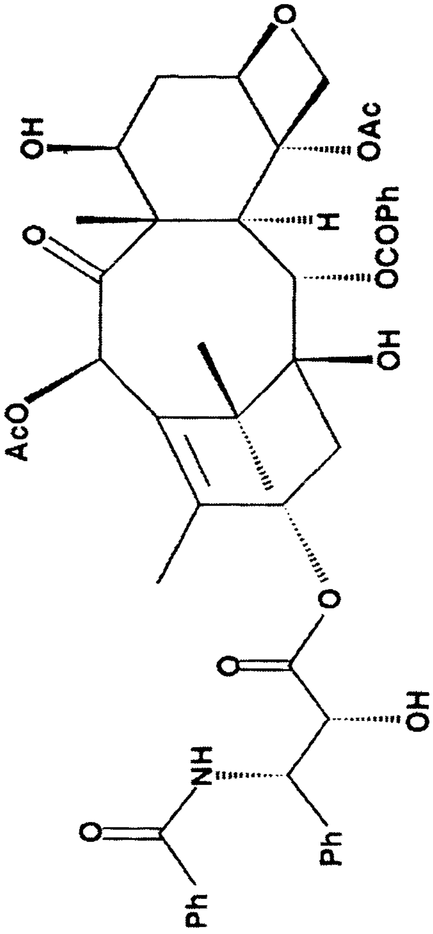
FIG. 4 shows the structure of Taxol.

In addition the antigen-binding site, the Ab can comprise a linker. The linker can be any moiety covalently bound to the portion of the Ab containing the antigen-binding site and capable of associating with the $C_n$. In one embodiment, the association involves a specific physical interaction between the linker and the $C_n$. For example, the linker can be an antibody raised against the $C_n$ to be used in the composition. An example of this embodiment is schematically represented in FIG. 1, wherein one or more $C_{60}$ fullerenes 10 are linked to an antitumor antibody 20 by an anti-$C_{60}$ antibody 30 associated with the antitumor antibody 20 by covalent or noncovalent interactions. In another embodiment, the association can be covalent. The linker can be formed by, for example, (i) substituting the $C_n$ with a sulfhydryl-containing (—SH) substituent; (ii) preparing an Ab with a sulfhydryl-containing linker; and (iii) reacting the Ab and the $C_n$ to form a —S—S— (disulfide) bond between the Ab and the $C_n$. An example of this embodiment is schematically represented in FIG. 2, wherein a $C_{60}$ fullerene 40 is linked to an antitumor antibody 50 via a disulfide bond 60.

In addition to the antibodies described above, any other compound that can recognize a specific antigen can be used as the Ab described herein. Such other compounds include antibody fragments and certain synthetic peptides that are known or are discovered to recognize specific antigens, as well as other targeting bioagents. Such other compounds can further comprise linkers, as described above.

The $C_n$ can itself be therapeutic. For example, fullerenes have strong antioxidant properties, and thus, they can be sufficient to treat oxidative stress diseases, by which is meant diseases that involve reactions by free radicals, such as reactive oxygen species, on subcellular structures, cells, tissues, organs, or organ systems. Exemplary oxidative stress diseases include neurodegenerative diseases, such as Alzheimer's disease, Parkinson's disease, and ALS; proliferation of T-lymphoid leukemia, at least some other cancer cells, and smooth muscle cells; atherosclerosis; ischemia reperfusion; and acute pancreatitis, among others.

In addition to the $C_n$-Ab, the composition can further comprise one or more other compounds. In one embodiment, the composition can further comprise a pharmaceutically-acceptable carrier. A "pharmaceutically-acceptable carrier" is a compound in which the $C_n$-Ab can be dissolved, suspended, emulsified, mixed, or otherwise combined with. Further, the carrier is generally safe when administered to a mammal. Exemplary pharmaceutically-acceptable carriers include, but are not limited to, water, buffered aqueous solutions, sucrose, and gelatin, among others.

As stated above, the $C_n$-Ab itself, or combined with a pharmaceutically-acceptable carrier, can be therapeutically beneficial to a mammal suffering from a disease, such as an oxidative stress disease wherein the $C_n$ core of the $C_n$-Ab can scavenge free radicals. Regardless of whether the $C_n$-Ab itself provides therapeutic benefit in treating a particular disease, the composition can further comprise a therapeutic molecule associated with the $C_n$-Ab.

A "therapeutic molecule" or "therapeutic agent," as used herein, is any molecule that has a therapeutic or diagnostic benefit or a benefit in performing a therapeutic or diagnostic function. As used herein, "therapeutic molecule" can include molecules containing metal atoms, but does not include such molecules wherein the metal atoms are substantially radioisotopic ("substantially radioisotopic" refers to a population of metal atoms wherein more than about 1 mol % of the metal atoms are radioisotopes). Any therapeutic molecule, from any source, can be used. In one embodiment, therapeutic molecules can be derived from a plant, an animal, a bacterium, a fungus, a virus, or another organism. In one embodiment, therapeutic molecules can be synthesized by known chemical synthesis techniques.

The therapeutic molecule can treat any disease. Exemplary diseases include, but are not limited to, cancers, autoimmune diseases, infections, liver diseases, and neurological diseases, among many others.

In one embodiment, the therapeutic molecule is an anti-cancer drug. Examples of anti-cancer drugs include paclitaxel (commercially available as Taxol, Bristol-Myers Squibb), doxorubicin (also known under the trade name Adriamycin), vincristine (known under the trade names Oncovin, Vincasar PES, and Vincrex), actinomycin D, altretamine, asparaginase, bleomycin, busulphan, capecitabine, carboplatin, carmustine, chlorambucil, cisplatin, cyclophosphamide, cytarabine, dacarbazine, daunorubicin, epirubicin, etoposide, fludarabine, fluorouracil, gemcitabine, hydroxyurea, idarubicin, ifosfamide, irinotecan, lomustine, melphalan, mercaptopurine, methotrexate, mitomycin, mitozantrone, oxaliplatin, procarbazine, steroids, streptozocin, taxotere, tamozolomide, thioguanine, thiotepa, tomudex, topotecan, treosulfan, UFT (uracil-tegufur), vinblastine, and vindesine, among others.

Other drugs include, but are not limited to, the following: hydrocodone, atorvastatin, estrogen, atenolol, levothyroxine, azithromycin, furosemide, amoxicillin, amlodipine, alprazolam, albuterol, loratadine, hydrochlorothiazide, omeprazole, sertraline, paroxetine, triamterene, lansoprazole, ibuprofen, celecoxib, simvastatin, cephalexin, metformin, rofecoxib, lisinopril, amoxicillin, clavulanate, propoxyphene, progesterone, prednisone, norgestimate, ethinyl estradiol, acetaminophen, codeine, cetirizine, fexofenadine, levothyroxine, amoxicillin, metoprolol, lorazepam, metoprolol, fluoxetine, ranitidine, zolpidem, citalopram, amitriptyline, alendronate, quinapril, sildenafil citrate, pravastatin, naproxen, gabapentin, warfarin, ciprofloxacin, verapamil, digoxin, albuterol, bupropion, lisinopril, clonazepam, tramadol, cyclobenzaprine, trazodone, fluticasone, montelukast, diazepam, isosorbide mononitrate s.a., glyburide, venlafaxine, levofloxacin, medroxyprogesterone, amoxicillin, fluconazole, enalapril, warfarin, carisoprodol, trimeth, sulfameth, fluticasone propionate, benazepril, mometasone, doxycycline, estradiol, allopurinol, rosiglitazone maleate, clopidogrel, propranolol, amlodipine, benazepril, methylprednisolone, valsartan, losartan, insulin, clonidine, diltiazem, loratidine, pseudoephedrine, latanoprost, pioglitazone, loratidine, pseudoephedrine, risperidone, fexofenadine, pseudoephedrine, doxazosin, raloxifene, norethindrone, folic acid, penicillin, oxycodone, temazepam, diltiazem, salmeterol, fosinopril, oxycodone, ramipril, promethazine, terazosin, olanzapine, gemfibrozil, levothyroxine, norethindrone, sumatriptan, hydroxyzine, meclizine, losartan, rabeprazole, phenyloin, clarithromycin, glimepiride, pantoprazole, spironolactone, ipratropium, albuterol, tamsulosin, lisinopril, metoclopramide, minocycline, bisoprolol, digoxin, valsartan, metronidazole, cefprozil, triamcinolone, glipizide, norethindrone, levonorgestrel, cefuroxime, nystatin, captopril, promethazine, codeine, acyclovir, norgestimate, oxycodone, irbesartan, nefazodone, mirtazapine, valacyclovir, methylphenidate, cerivastatin, fluoxetine, nitrofurantoin, loratadine, glyburide, metformin, metformin, diltiazem, desogestrel, mupirocin, 1-norgestrel, fluvastatin, aspirin, clarithromycin, clindamycin, esomeprazole, metaxalone, nortriptyline, cimetidine, fenofibrate, iprotropium bromide, tamoxifen, calcitonin salmon, felodipine, levonorgestrel, salmeterol, fluticasone, theophylline, tetracycline, tolterodine, gatifloxacin, nifedipine, diclofenac, triamcinolone acetonide, promethazine, indomethacin, benzonatate, phenobarbital, naproxen sodium, mometasone, hydrocodone, glipizide, divalproex, nitroglycerin, and phenazopyridine, among others.

The therapeutic molecule can be a diagnostic agent, such as an MRI contrast agent (e.g., a magnetic metal particle), a CT contrast agent (e.g., a hyperpolarized gas), an X-ray contrast agent, a nucleoscan contrast agent, or an ultrasonic contrast agent, among others.

The therapeutic molecule can be a molecule that assists in the performance of a therapeutic or diagnostic technique. In one embodiment, the therapeutic molecule is a sedating drug.

One or more therapeutic molecules can be used in any composition or method of the present invention.

The therapeutic molecule can be associated with the $C_n$-Ab by one or more routes of association. The association can be a covalent link between the fullerene or nanotube core and the therapeutic molecule; a covalent link between a substituent of the fullerene or nanotube, if any, and the therapeutic molecule; a non-covalent favorable van der Waals interaction; an ionic association between a positively- or negatively-charged group on a substituent of the fullerene or nanotube and an oppositely-charged group on the therapeutic molecule; or the encapsulation of the therapeutic molecule in the fullerene or nanotube core, among others.

A covalent link can be direct or it can make use of a covalent linker linking the therapeutic molecule and the fullerene or nanotube core or substituent, if any, of the fullerene or nanotube. In one embodiment, the covalent link can be cleavable by an appropriate cleaving technique, such as photolysis, enzymatic cleavage, or chemical cleavage, among others. In another embodiment, a non-covalent association between the therapeutic molecule and the fullerene or nanotube can be dissociated by application of an appropriate chemical, e.g., when the association is an ionic association, the association can be dissociated by application of a charged compound of the same charge as the charged group on the therapeutic molecule. Other techniques for dissociating a non-covalent association between the substituted fullerene or nanotube and the therapeutic molecule will be apparent to one of ordinary skill in the art in light of the present specification. A chemical or enzyme used to promote dissociation can be referred to as an "adjuvant." In another embodiment, the therapeutic molecule is covalently linked to the fullerene or nanotube and is not dissociated therefrom.

Any compound that can be attached to or enclosed within the $C_n$ and that would be expected to have a therapeutic benefit when delivered to a specific tissue or cell type is a therapeutic molecule within the scope of the present claims. Whether a compound is expected to have a therapeutic benefit will depend on the specific tissue or cell type; the Ab attached to the $C_n$; and other factors apparent to one of ordinary skill in the art.

If a therapeutic molecule is present, the order in which the therapeutic molecule and the Ab are associated with the $C_n$ is not crucial.

In one embodiment, the therapeutic molecule can be associated with the $C_n$-Ab by association with a "buckysome," as described by Hirsch et al., U.S. Pat. Appln. 10/367,646, filed Feb. 14, 2003, the disclosure of which is herein incorporated by reference. A "buckysome" is a liposome-like structure comprising an amphiphilic fullerene, which is a substituted fullerene comprising both one or more hydrophilic substituents and one or more hydrophobic substituents.

The composition can further comprise one or more additional compounds not enumerated above, whose inclusion in compositions comprising $C_n$-Ab or useful in the methods described below is a matter of routine experimentation for an ordinary skilled artisan having the benefit of the present disclosure.

In another embodiment, the present invention relates to a method of treating a disease in a mammal, comprising:

administering to the mammal an effective amount of a composition comprising (i) a $C_n$-Ab, wherein $C_n$ is a fullerene or nanotube comprising n carbon atoms, and Ab is a moiety comprising an antigen-binding site and is linked to the Cn and (ii) a pharmaceutically-acceptable carrier.

The composition has been described above, and can comprise further compounds, such as therapeutic molecule associated with the $C_n$-Ab, among others as described above.

"Treat," or variations thereof, when used in this context, refers to the reduction or elimination of the symptoms of a disease or the diagnosis of a disease.

Any mammal can be a recipient of the administered composition according to this method. In one embodiment, the mammal is a human. In another embodiment, the mammal is a non-human mammal which provides economic, research, or esthetic utility to humans. Examples of such non-human mammals include, but are not limited to, cattle, horses, sheep, goats, monkeys, apes, rats, mice, dogs, and cats, among others.

In one embodiment, the disease is an oxidative stress disease, by which is meant a disease of one or more tissues, tissue types, organs, or organ systems, caused by oxidizing agents, such as free radicals, particular radical oxygen species. The disease can lead to such symptoms as one or more of damage to intracellular components; death or morbidity of cells; or failure of tissues, organs, or organ systems. Oxidative stress diseases can be chronic or acute, and can arise from by-processes of metabolism, irritation by chemicals in the environment (for example, tobacco smoke), or internal challenge (for example, neural ischemia), among others. In one embodiment, the oxidative stress disease is a neurological disease, by which is meant a disease of neurons, neural tissue, or the central nervous system.

The $C_n$-Ab can be administered either systemically or locally. Appropriate routes for systemic administration include, but are not limited to, intravenously, orally, nasally, or rectally, among others. Appropriate routes for local administration include, but are not limited to, subcutaneously or transdermally, among others. The inclusion of an antigen-binding site in the $C_n$-Ab allows a systemic administration to provide localization to cells, tissues, organs, or organ systems wherein the antigen recognized by the antigen-binding site of the $C_n$-Ab is present.

The $C_n$-Ab can be administered at any appropriate dosage which provides to the mammal an amount of the $C_n$ effective to treat the oxidative stress disease. In one embodiment, the composition is administered at a dosage of from about 0.001 mg $C_n$ per kg body weight per day to about 1 g $C_n$ per kg body weight per day.

In one embodiment, the disease is any disease which can be treated by a drug. The drug can upregulate or downregulate one or more metabolic processes in healthy cells, unhealthy cells, tumor cells, parasites, bacteria, or other infectious agents, in order to reduce or eliminate effects detrimental to the health of the mammal or increase effects beneficial to the health of the mammal resulting from the metabolic process or processes. The disease can lead to such symptoms as one or more of damage to intracellular components; death or morbidity of cells; or failure of tissues, organs, or organ systems. The disease can be chronic or acute, and can arise from infection, exposure to agents in the environment, autoimmune response, or genetic defect, among others. In one embodiment, the disease is a cancer, by which is meant a disease in which malignant cells arise within the mammal.

The composition can be administered either systemically or locally. Appropriate routes for systemic administration include, but are not limited to, intravenously, orally, nasally, or rectally, among others. Appropriate routes for local administration include, but are not limited to, subcutaneously or transdermally, among others. The inclusion of an antigen-binding site in the $C_n$-Ab allows a systemic administration to provide localization to cells, tissues, organs, or organ systems wherein the antigen recognized by the antigen-binding site of the $C_n$-Ab is present.

The composition can be administered at any appropriate dosage which provides to the mammal an amount of the therapeutic molecule effective to treat the disease. In one embodiment, the composition is administered at a dosage of from about 0.001 mg therapeutic molecule per kg body weight per day to about 1 g therapeutic molecule per kg body weight per day.

The composition can provide therapeutic benefit both by delivering a therapeutic molecule to a particular cell, tissue, organ, or organ system and by scavenging reactive oxygen and other free radical species by antioxidant reactions at the $C_n$ core.

The method can further comprise administering an adjuvant to the mammal, wherein the adjuvant dissociates the therapeutic molecule from the $C_n$-Ab. The adjuvant can be a chemical or an enzyme capable of specifically cleaving the linkage, if any, between the therapeutic molecule and the $C_n$-Ab. The adjuvant can be an energy source, such as heat, light, ultrasound, or another energy source which emits energy sufficient to cleave a linkage between the therapeutic molecule and the $C_n$-Ab. The ordinary skilled artisan can determine other adjuvants as a matter of routine experimentation in light of the present disclosure.

The invention described herein presents a novel methodology for controlled-drug release using nanometric liposomes containing amphiphilic fullerene derivatives. In the presence of conventional liposome-forming lipids, therapeutic agents and functionalized amphifullerenes can be entrapped within the bilayer membrane under specific pH and temperature control to form "buckysomes." Similarly, the therapeutic agents can be entrapped within the carbon cage of the fullerene. The buckysome can include a $C_n$-Ab structure, such as an Ab covalently linked to a fullerene core or a substituent group, such as a hydrophilic substituent group, of a substituted fullerene.

One particular use of this invention is to induce sleep in patients who inhale aerosolized, nanometric liposomes containing sedating drugs. Under normal physiologic conditions (pH=7.35-7.45, T=37-38° C.), the sedating drugs diffuse through the lipid bilayer and into the bloodstream. As the patient becomes sedated, the decreasing blood temperature slows down the diffusive release of the drug. Furthermore, the resulting decline in blood pH as the patient enters deep sleep forces discontinuation of drug release. This method of delivering sedating agents to the bloodstream will be unique in that it will minimize the possibility of overdose, ensuring safe drug delivery. Because of the temperature and pH dependence of the drug's release, therapeutic delivery is controlled homeostatically by the individual. Currently, sedating agents are delivered intravenously or by direct inhalation, where dosage levels must be controlled externally by the administering person in order to prevent harmful overdose. This unique method of drug delivery is controlled by the patient's body temperature and pH. Under normal physiologic conditions, T and pH are at levels that facilitate drug delivery. After sedation, drug activity is "turned off" as body T and pH decrease. Current methods of drug administration do not possess this capability.

For therapeutic applications, buckysomes can be employed for targeted drug delivery to physiological areas of concern. Conjugation of buckysomes with antibodies specific to regions of interest can effectively ensure precise delivery of the drug-transporting vehicles to where therapeutic intervention is necessary. For example, buckysomes may be functionalized with antibodies specific to regions of atherosclerotic plaque or cancer.

An additional application of this innovative technology is the controlled delivery of contrast agents employed in imaging applications. By anchoring tissue- and/or site-specific antibodies to the amphifullerenes, accumulation of the immunospecific liposomes in regions of interest can be initiated. Entrapped within the fullerene cages can be diagnostic agents, such as MRI contrast agents (e.g., magnetic metal particles), CT contrast agents (e.g., hyperpolarized gas), X-ray contrast agents, nucleoscan contrast agents, and ultrasonic contrast agents, among others. Furthermore, therapeutic agents can be incorporated in the liposomal complex, offering a methodology for site-specific, disease identification and therapy within the body.

In one embodiment, the present invention relates to a method for delivering therapeutic agents using nanometric liposomes, wherein the therapeutic agents can be located on the surface of the liposome, between layers of the liposome, or entrapped within the liposome. In one embodiment, the liposomes remain intact below pH=7 and T=37° C. In another embodiment, the therapeutic agents remain entrapped within the liposomes below pH=7 and T=37° C. In a further embodiment, the therapeutic agents are diffusively released at or above pH=7.3 and T=37° C. In yet another embodiment, the liposomes are delivered as an aerosol suitable for inhalation. In yet a further embodiment, the therapeutic agents are sedating agents.

In one embodiment, the present invention relates to a method for delivering contrast agents for imaging applications to sites of interest within the body using nanometric liposomes, wherein the contrast agents can be located on the surface of the liposome, between layers of the liposome, or entrapped within the liposome. In one embodiment, the therapeutic agents are entrapped within the liposomes and diffusively released in the region of interest.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Targeting Fullerenes Using Recombinant Antibody Constructs

Background

Monoclonal antibody (MAb)-based procedures have traditionally been used in the diagnosis and therapy of human cancers. However, clinical use of these agents has met with limited success due to drawbacks associated with this approach, e.g. heterogeneity of antigen expression, poor tumor penetration into solid tumors due in part to antibody size, and antigenicity of the antibodies (Roselli et al., *In Vivo,* 7: 615-621 (1993); Berkower, *Current Opin. Biotechnol.,* 7: 622-628 (1996); Pullyblank et al., *Brit. J. Surg.,* 84: 1511-1517 (1997); Panchagnula et al., *J. Clin. Pharm. & Therapeutics,* 22: 7-19 (1997); Pancha, *Biochem. Pharmacol.,* 55: 247-252, (1998)). To circumvent these problems, a number of molecular approaches have been applied to reconfigure the conventional antibody structure into mouse:human chimeras, completely human antibodies or reshaped antibody fragments containing the antigen-binding portions of the original structure in a smaller and simpler (single-chain) format (Bird et al., *Science,* 242: 423-426 (1988) [published erratum: *Science* 244: 409 (1989)]; Kipriyanov et al., *Molec. Immunol.* 31: 1047-1058 (1994); Owens et al., *J. Immunol. Methods,* 168: 149-165 (1994); McCartney et al., *Protein Eng.,* 8: 301-314 (1995); Worn et al., *Biochemistry,* 22: 13120-13127 (1998)). Single-chain antibodies (scfv, sfv), retaining the binding characteristics of the parent immunoglobulin (IgG), consist of the antibody $V_L$ and $V_H$ domains linked by a designed flexible peptide linker (Weis et al., *J. Steroid Biochem. & Molec. Biol.,* 43: 1-7 (1992); Kurucz et al., *Proc. Natl. Acad. Sci.,* 90: 3830-3834 (1993)). Furthermore, scfvs may be preferred in clinical and diagnostic applications currently involving conventional MAbs or Fab fragments thereof, since their smaller size may allow better penetration of tumor tissue, improved pharmacokinetics, and a reduction in the immunogenicity observed with intravenously administered murine antibodies.

Among the few target antigens that are expressed at high levels in melanoma cells compared to normal tissue is the surface domain of a high molecular weight glycoprotein (gp240) found on a majority of melanoma cell lines and fresh tumor samples (Kantor et al., *Hybridoma,* 1: 473-482 (1982)). Two murine antibodies (designated 9.2.27 and ZME-018) recognizing different epitopes on this antigen have been previously isolated and described (Morgan et al., *Hybridoma,* 1: 27-36 (1981); Wilson et al., *Int. J. Cancer,* 28: 293-300 (1981)). The murine monoclonal antibody ZME-018 possesses high specificity for melanoma and is minimally reactive with a variety of normal tissues, making it a promising-candidate for further study. Clinical trials examining the ability of this antibody to localize within melanoma lesions have demonstrated selective concentration in metastatic tumors (Macey et al., *Am. J. of Physiologic Imaging,* 3: 1-6 (1988); Koizumi et al., *Jap. J. Cancer Res.,* 79: 973-981 (1988)).

Successful development of tumor-targeted therapeutic agents is dependant, in part, on the site-specific delivery of therapeutic agents and also on the biological activity of the delivered agent. Monoclonal antibodies have been employed to impart selectivity to otherwise indiscriminately cytotoxic agents such as toxins, radionuclides, and growth factors (Williams et al., *Cancer Res.,* 50: 974s-979s (1990); Rowlinson-Busza et al., *Current Opin. Oncol.,* 4: 1142-1148 (1992); Wahl, *Cancer,* 73: 989-992 (1994)). The present study describes our investigation of a recombinant construct consisting of a single-chain analog of the antibody ZME-018 (cloned $V_H$ and $V_L$ domains) chemically fused to a chemically modified fullerenes. The recombinant antibody is engineered to contain a specific linker terminating in an amino acid molecule with properties specifically suitable for conjugation to the fullerene molecule. An example of the first such linkage will be a disulfide link between modified fullerene and a terminal cysteine amino acid.

Materials

The cDNA encoding antibody ZME-018 was amplified from hybridoma RNA obtained from hybridoma cells expressing the murine antibody using kits from Novagen (Madison, Wis.) and Invitrogen Corp. (Carlsbad, Calif.). The PCR reagents were obtained from Fisher Scientific (Pittsburgh, Pa.), the molecular biology enzymes were purchased from either Boehringer Mannheim (Indianapolis, Ind.) or New England Biolabs (Beverly, Mass.). Bacterial strains and pEt bacterial expression plasmids were obtained from Novagen (Madison, Wis.) and growth media was purchased from Difco Laboratories (Detroit, Mich.). All other chemicals and reagents were either from Fisher Scientific or Sigma Chemical Co. (St. Louis, Mo.). Metal affinity resin (Talon) was obtained from Clontech Laboratories (Palo Alto, Calif.). Other chromatography resins and materials were from Pharmacia Biotech (Piscataway, N.J.). Tissue culture reagents were from GIBCO BRL (Gaithersburg, Md.). All DNA sequencing was performed at the M. D. Anderson Cancer Center Core Facility.

Methods

Cloning of the $V_H$ and $V_L$ Domains of Antibody ZME-018

Messenger RNA from murine hybridoma FMT 112 P2 expressing antibody ZME-018 (IgG2A) was isolated using the Invitrogen Fast Track kit and transcribed to cDNA with the Invitrogen Copy Kit using the specified conditions. Amplification of antibody light and heavy chain variable regions was carried out using the Novagen Ig-Prime kit with the mouse Ig-primer set. The PCR profile for light-chain amplification was as follows: 30 cycles of 94° C.×1 min, 60° C.×1 min, and 72° C.×1 min terminated by a 5 min incubation at 72° C. For heavy-chain reactions, the identical conditions were used except that the annealing temperature was 50° C. instead of 60° C. DNA amplified using this procedure was then cloned into the Invitrogen T/A cloning vector pCR II without further purification, transformed into *E. coli* XL1-Blue, and identified using blue-white screening procedures. Positive clones (five each from the heavy-and light-chain libraries) were sequenced using the T-7 and SP6 promoter primers and antibody domains identified by homology to other immunoglobulin sequences.

Construction of Genes Encoding the Single-Chain Antibody scfvMEL Containing the Terminal $G_4S$ Linker with a Terminal Cysteine A two-step splice-overlap extension PCR method (Sambrook et al., Molecular Cloning: A Laboratory Manual, 2nd Edition, Cold Spring Harbor Laboratory Press, Cold Spring Harbor, N.Y. (1989)) was used to construct the single-chain antibody ZME-018 using light-and heavy-chain DNA clones as templates. Light-chain sequences were amplified using the primers A (5'-GCTGCCCAACCAGCC ATGGCGGACATTGTGATG-3') and C (5'-GCCGGAGCCTGGCTTGC(A/C) GCTGCCGCTGGIGGAGCCTTTGATC(A/T)CCAG -3'), whereas heavy-chain DNA was amplified with the primers B (5'-AAGCCAGGCTCCGGCGAAGGCAGCACCAAAGG CGAAGTGAAGGTT-3') and D (5'-GCCACCGCCACCACTAGTTGAGGAGACTGT-3'). The PCR profiles for each set of reactions were as follows: 30 cycles of 1-min denaturation at 94° C., 1 min annealing at 50° C., and a 1 min extension at 72° C., followed by a final 5-min incubation at 72° C. One-tenth volume of each of these reactions were combined and used directly in a second PCR with only primers A and D following the same reaction profile as before. The final product was purified using Geneclean II (Bio 101, Vista, Calif.), digested with the restriction enzymes Nco I and Spe I, and cloned into the T-7-based plasmid vector pET-22b. The genes encoding scfvMEL and recombinant gelonin were fused together using the splice-overlap extension PCR method with antibody and gelonin DNA as templates and primers NbsphZME (5'GGCGGTGGCTCCGTCATGACGGACATTGTGATGACCCAGTCT CAAAAATTC-3'), primer NTXOM (5'-GGTGGCGGTGGCTCCGGTCTAGACACCGTGACG-3'), and primer XOMBAC (5'-AAGGCTCGTGTCGACCTCGAGTCATTAAGC TTTAGGATCTTTATC-3'). Purified PCR products were then purified and digested as before and cloned into the vector pET-32a. Sequenced DNA clones were subsequently transformed into *E. coli* strain AD494(DE3) pLys S obtained from Novagen for expression of the recombinant construct.

Protein Expression in *E. coli*

To express the recombinant antibody, bacterial cultures were incubated at 37° C. in 2xYT growth medium with strong antibiotic selection (200 μg/ml ampicillin, 70 μg/ml chloramphenicol, and 15 μg/ml of kanamycin) and grown until early log phase ($A_{600}$=0.4-0.8). The cultures were then diluted 1:1 with fresh 2xYT medium containing the same concentrations of antibiotics, and target protein expression was induced at 23° C. by the addition of 0.1 mM IPTG for 16-23 h. Induced bacterial cultures were then centrifuged and stored frozen at −80° C. for later purification.

Frozen bacterial pellets from induced cultures expressing scFvZME/linker were thawed at room temperature and lysed by the addition of 1 mg/ml lysozyme in 10 mM Tris-HCl, pH 8.0 for 30 min at 4° C. The bacterial lysates were then sonicated three times for 10 sec each with a cell disruptor and centrifuged at 14,000 rpm for 30 min at 4° C. The supernatant was transferred and saved on ice, and the sonication procedure was repeated with the cell pellet. Supernatants from the two lysates were then combined and ultracentrifuged at 40,000 rpm in a SS-34 rotor for 45 min at 4° C. The samples containing only soluble protein were then filtered (0.22 μm pores), adjusted to 40 mM Tris-HCl with 1M Tris-HCl (pH 8.0), and then loaded at room temperature onto a Talon metal-affinity column pre-equilibrated with the same buffer. After loading, the column was washed with 3 column volumes of loading buffer, followed by a 5-column volume wash with 40 mM Tris-HCl pH 8.0, 500 mM NaCl, and 5 mM imidazole. Bound protein was then eluted with 5 column volumes of buffer containing 40 mM Tris-HCl (pH 8.0), 500 mM NaCl and 100-200 mM imidazole. Fractions containing antibody/linker fusion were combined, quantitated, and dialyzed into 20 mM Tris-HCl (pH 7.2), 50 mM NaCl prior to digestion with enterokinase to remove the 6×His tag using the procedure established by Novagen (Madison, Wis.).

Results

The genes encoding the antibody and $G_4S$-C linker fragments were linked together using a PCR-based method to construct a fusion in the antibody-linker orientation. The gene fusion gene was also C-terminal tagged with a hexahistidine sequence and expressed in *E. coli* AD494(DE3) pLysS using the Novagen T-7-based expression vector pET-32b.

The antibody was constructed to encode the light chain variable region ($V_L$) at the N-terminus of the protein with an 18 amino acid flexible peptide linker (Stirpe et al., *J. Biol. Chem.* 255: 6947-6953 (1992)) with the $V_H$ C-terminus. The $G_4S$-C linker(Glycine-Glycine-Glycine-Glycine-Serine-Cysteine) was positioned downstream of the $V_H$. We chose this configuration for reasons involving the unhindered flexibility of the antibody-binding site. DNA-sequencing studies of the final fusion protein confirmed the sequence of the final product and that no errors had been introduced using this PCR method. In addition, DNA sequencing also confirmed that the target gene was inserted into the correct reading frame in the pET-32b vector.

The plasmid vector pET-32b containing the fusion gene was transformed into *E. coli* AD494(DE3) pLysS, and expression of the target protein was induced by the addition of ITPG. As seen in a coomassie-stained gel, a protein of the expected molecular mass (45 kDa) was induced. This protein was purified using IMAC resin, and the eluate was exposed to recombinant enterokinase (EK) to yield the final native fusion construct migrating as one band at 25 kDa. The fusion construct was also examined by Western blot using an anti-single-chain antibody.

Example 2

Figure 9:
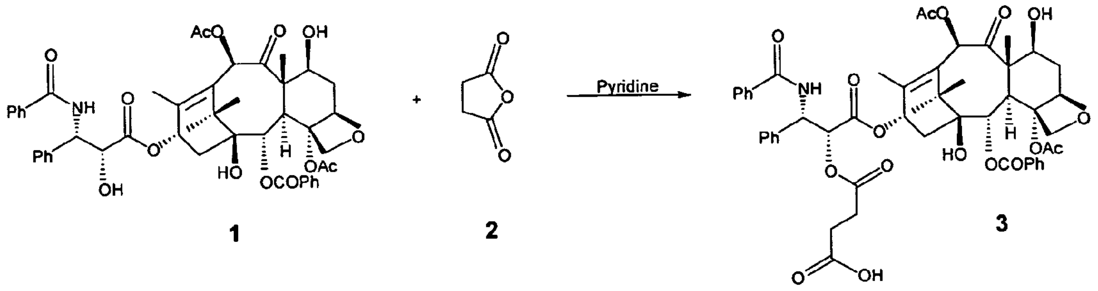
FIG. 9 shows a scheme for the synthesis of 2'-succinyl taxol (structure 3) from the reaction of taxol (structure 1) with succinic anhydride (structure 2).

Synthesis Scheme for the Production of a Cn with an Associated Therapeutic Molecule A synthetic approach to making a fullerene-taxol conjugate was developed. The 2'-OH group of taxol (structure 1) was chosen for modification since it is the most reactive hydroxyl group in the molecule. Thus, in the reaction of taxol with succinic anhydride (structure 2) 2'-succinyl taxol (structure 3) is formed (FIG. 9).

Figure 10:
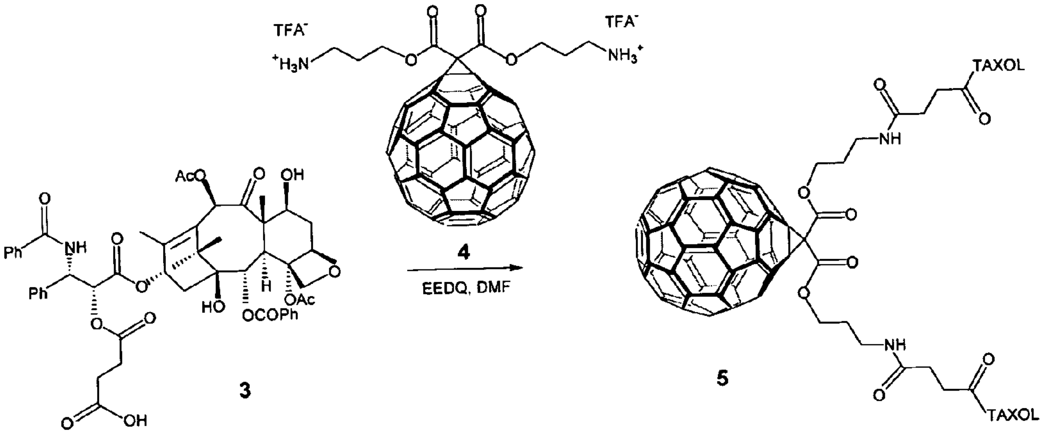
FIG. 10 shows a scheme for the attachment of 2'-Succinyl taxol to a fullerene by reaction with an amino-substituted methanofullerene derivative (structure 4).

2'-Succinyl taxol can be attached to a fullerene in a number of ways, the reaction with an amino-substituted methanofullerene derivative (structure 4) being one of the most promising (FIG. 10).

Experimental Procedures

Part I. Synthesis of Taxol Succinate (FIG. 9)

40 mg of taxol and 23.4 mg of succinic anhydride were dissolved in 10 mL of dry pyridine and stirred at room temperature for 2.5 hours. The solvent was removed under reduced pressure and the residue was treated with 15 mL of water, stirred for 20 minutes, and filtered. The precipitate was dissolved in acetone, water was slowly added, and white crystals of 2'-succinyl taxol were collected.

Part II. Synthesis of Amino-Substituted Methanofullerene

Figure 11:
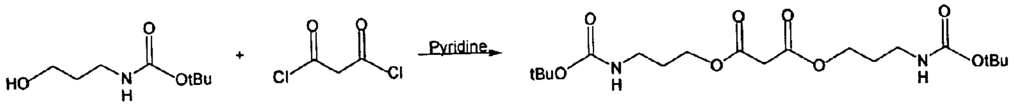
FIG. 11 shows a scheme for the synthesis of a malonate reagent (structure 8) from tert-butyl N-(3-hydroxypropyl) carbamate (structure 6) and malonyl dichloride (structure 7) in the presence of pyridine and dry $CH_2Cl_2$.
Figure 12:
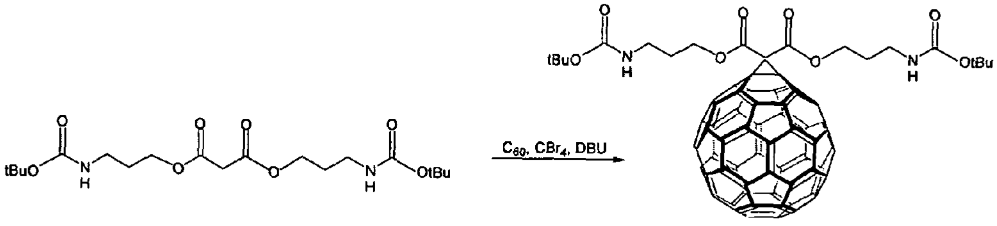
FIG. 12 shows a scheme for the synthesis of an N-protected amino-substituted methanofullerene derivative, by reacting $C_{60}$ fullerene with $CBr_4$ and the malonate reagent (structure 8), followed by addition of DBU, in toluene.

Starting from 5 g of tert-butyl N-(3-hydroxypropyl)carbamate (structure 6, as shown in FIG. 11, below), a malonate reagent (structure 8) was prepared by reacting 1.97 g of malonyl dichloride (structure 7) and 2.21 g of pyridine in dry $CH_2Cl_2$ as previously reported (Richardson, C.; Schuster, D.; Wilson, S. *Organic Letters* 2000, 2, 1011-1014). The crude reaction mixture was chromatographed on silica gel with 1:1 hexane/ethyl acetate to isolate the malonate reagent. To prepare an N-protected amino-substituted methanofullerene derivative, the method of Hirsch for the in situ generation of the active brominated intermediate was used (FIG. 12) (Camps, X.; Hirsch, A. *J. Chem. Soc., Perkin Trans.* 11997, 1595-1596). Accordingly, 500 mg of $C_{60}$ was dissolved in 400 mL of toluene and mixed with 114.9 mg of $CBr_4$ and 142.8 mg of the malonate reagent (structure 8), followed by addition of 105.0 mg of diazobicycloundecane (DBU). The reaction was complete in an hour and the solvent was removed under reduced pressure. The amino-substituted methanofullerene derivative product (structure 9) was purified by flash chromatography on a silica gel column with 2:1 toluene/ethyl acetate followed by HPLC in 4:1 toluene/ethyl acetate.

Figure 13:
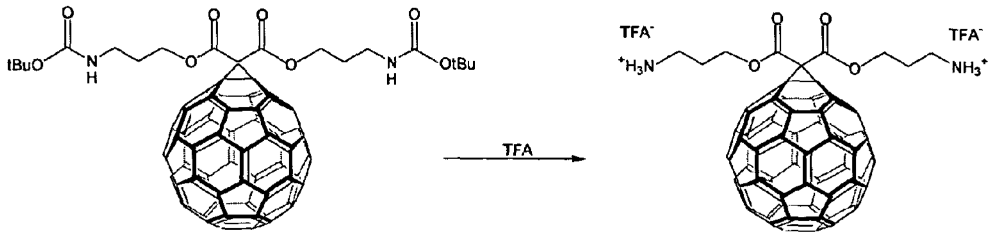
FIG. 13 shows a scheme for the deprotection of the amino groups in the amino-substituted methanofullerene derivative using trifluoroacetic acid.

Deprotection of amino groups was achieved using trifluoroacetic acid as shown in FIG. 13. 51.0 mg of structure 9 was dissolved in 100 ml of $CH_2Cl_2$ and an equal volume of trifluoroacetic acid (TFA) was added (FIG. 13), to yield TFA methanofullerene (structure 4). The solution was stirred for 30 minutes and the solvent was removed under reduced pressure.

Part III. The Reaction Between Taxol Succinate and Amino-Substituted Methanofullerene Derivative (FIG. 10)

44.0 mg of 2'-ethoxy-1'-ethoxycarbonyl-1,2-dihydroquiniline (EEDQ) were added to a solution of 85.6 mg of 2'-succinyl taxol in 2 mL of DMF. The solution was stirred for 30 minutes at room temperature and then added to 52.2 mg of TFA methanofullerene (structure 4) dissolved in 1 mL of DMF. The latter solution was stirred at ambient temperature for 4 hours and the solvent was removed under reduced pressure. The crude reaction mixture was chromatographed on a silica gel column with 90:10 chloroform/methanol to extract the taxol-methanofullerene product (structure 5, FIG. 10).

Example 3

Attachment of an Antibody to a Therapeutic Molecule-Fullerene

Figure 5:
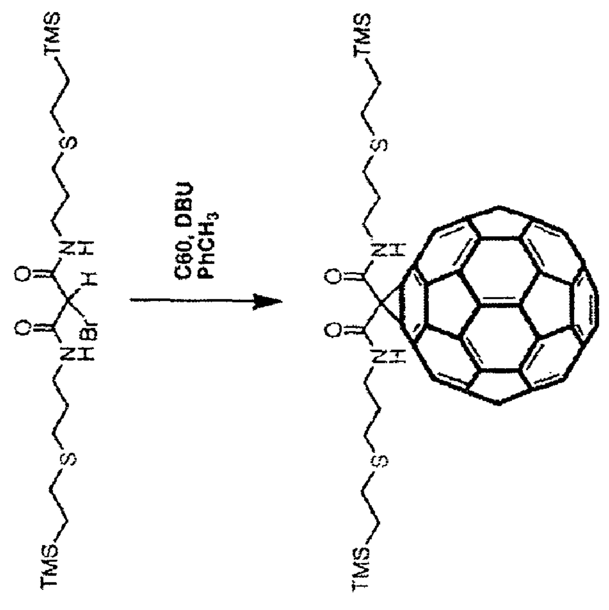
FIG. 5 shows a synthesis scheme for the production of a fullerene containing a protected thioldiamide malonate substituent.
Figure 6:
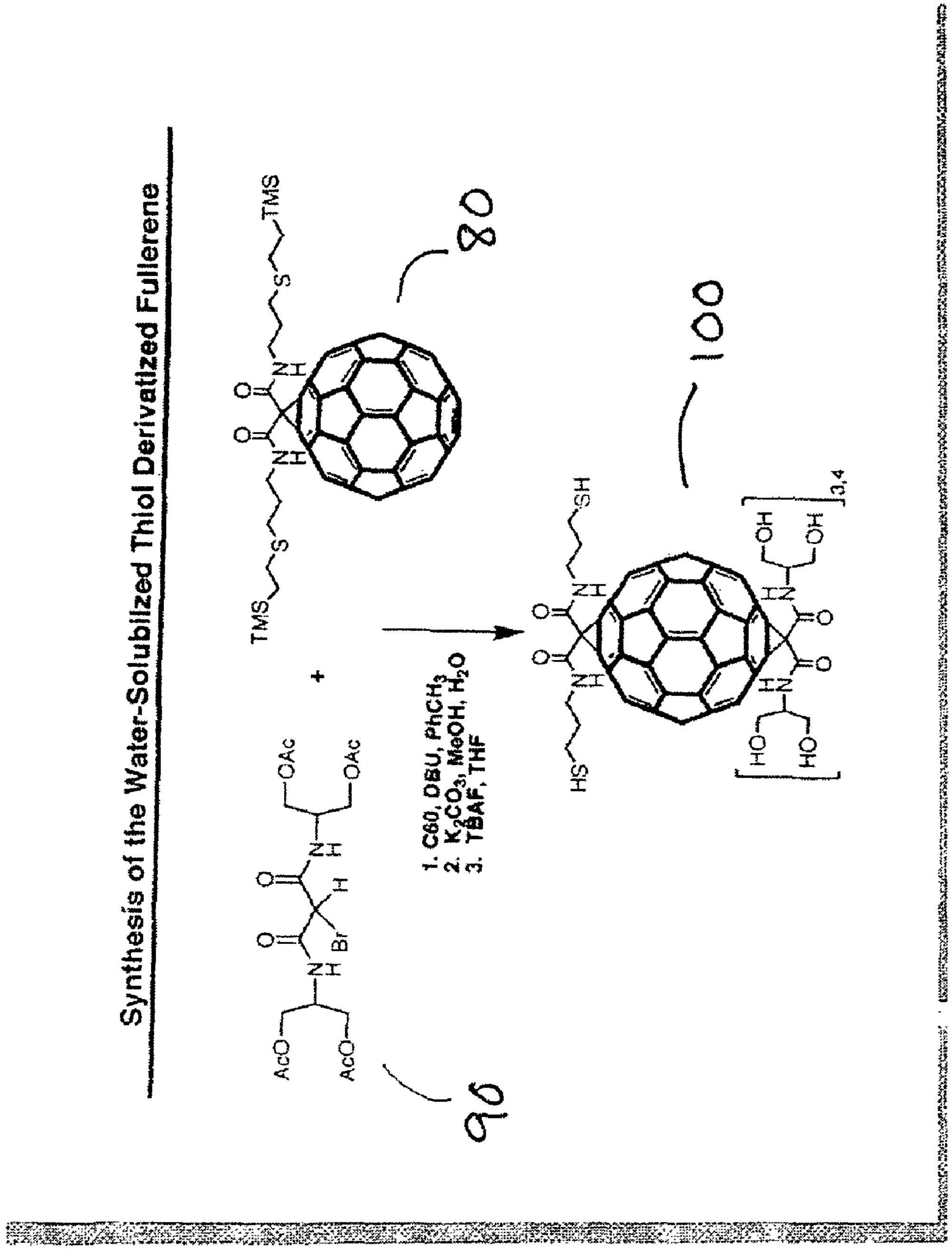
FIG. 6 shows a synthesis scheme for the production of a water-soluble thioldiamide malonate-substituted fullerene, starting with the product of the scheme shown in FIG. 5.
Figure 7:
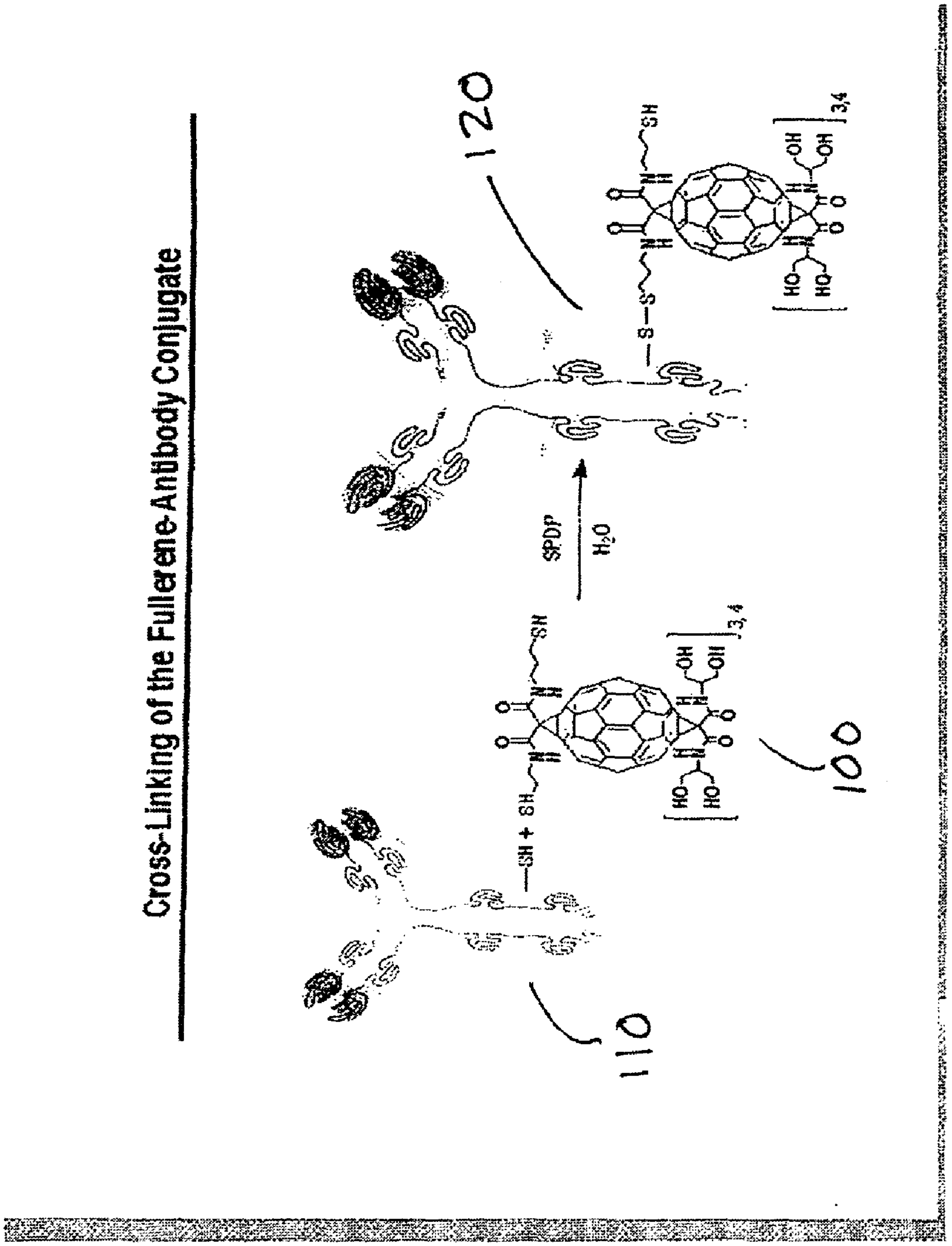
FIG. 7 shows a synthesis scheme for the production of a cross-linked $C_n$-Ab, starting with the product of the scheme shown in FIG. 6.
Figure 8:
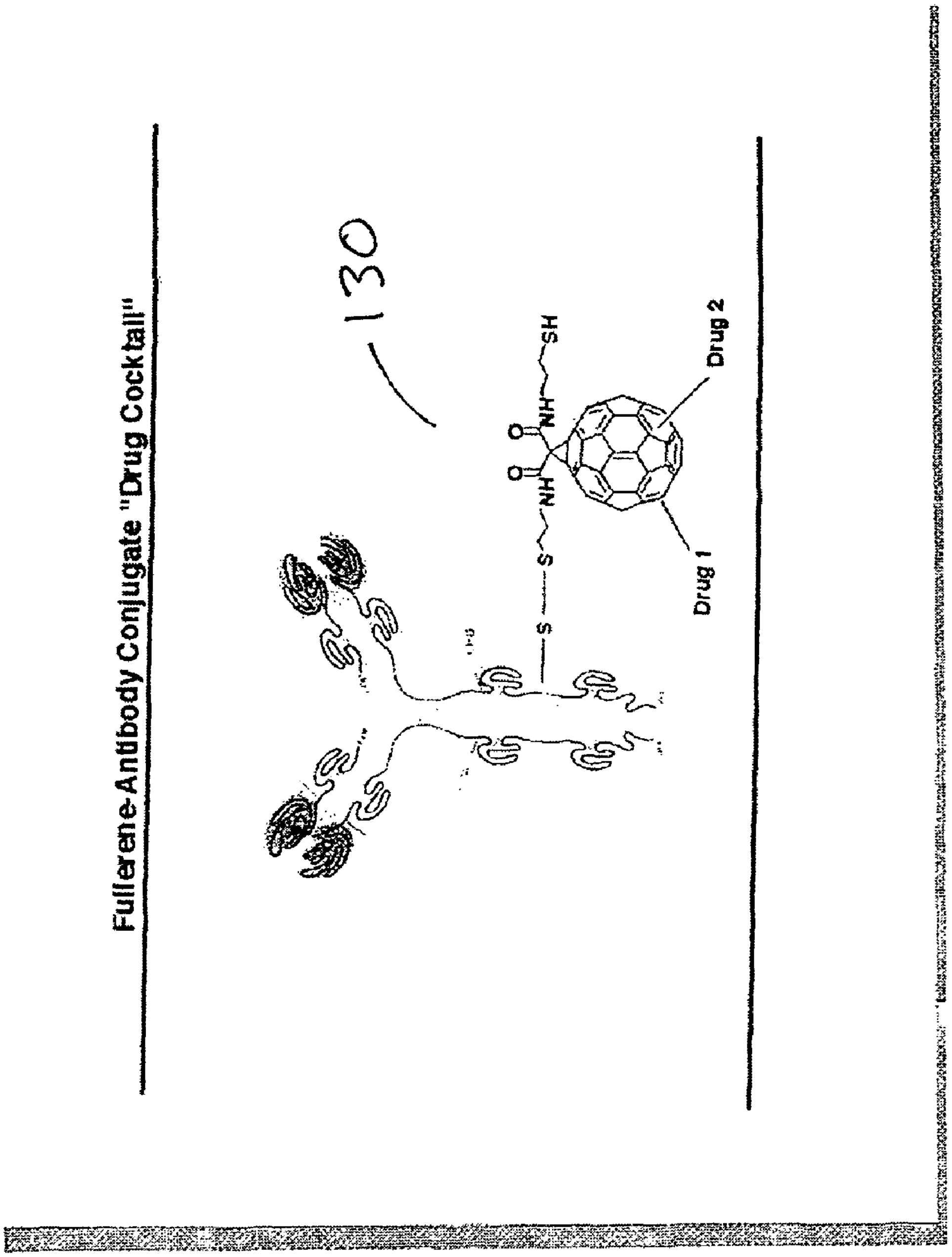
FIG. 8 represents a $C_n$-Ab comprising two therapeutic molecules.

As represented in FIGS. 5-8, a protected thioldiamide malonate substituent 70 can be added to a fullerene core to generate a protected thioldiamide malonate-substituted fullerene 80 (FIG. 5). The protected thioldiamide malonate-substituted fullerene 80 can then be made water-soluble by the scheme shown in FIG. 6, i.e., by deprotecting the thioldiamide malonate side chains to yield sulfhydryl groups and by substituting the fullerene with groups containing polar moieties 90 to yield the water-soluble thioldiamide malonate-substituted fullerene 100. Thereafter, an antibody 110 containing a cysteine amino acid having a sulfhydryl (—SH) side chain can be covalently linked to the thioldiamide malonate-substituted fullerene 100 across the sulfhydryl groups of the antibody and the thioldiamide malonate-substituted fullerene, to yield a product the same or similar to compound 120 shown in FIG. 7. Thereafter, one or more therapeutic molecules can be added to a fullerene core associated with an antibody, or a fullerene core prior to association with an antibody, to yield the product 130 shown in FIG. 8.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A composition, comprising:
   (i) a $C_n$-Ab, wherein $C_n$ is a fullerene or nanotube comprising n carbon atoms, and Ab is a moiety comprising an antigen-binding site and is covalently linked to the $C_n$, wherein the antigen-binding site recognizes an antigen associated with a medical condition; and (ii) a pharmaceutically-acceptable carrier.

2. The composition of claim 1, wherein the $C_n$ is substituted with one or more water-solubilizing groups.

3. The composition of claim 1, wherein the Ab comprises an antigen-binding site selected from ZME-018, SCFVMEL, dSCFVMEL, GD2, HuM195, herceptin, BACH 250, ML 3-9, C 6.5, or αMMP9.

4. The composition of claim 1, further comprising a therapeutic molecule associated with the $C_n$-Ab.

5. The composition of claim 4, wherein the therapeutic molecule is covalently bound to the $C_n$.

6. The composition of claim 4, wherein the $C_n$ is substituted with a polar group and the therapeutic molecule is associated with the polar group.

7. The composition of claim 4, wherein the therapeutic molecule is paclitaxel, doxorubicin, vincristine, or cisplatin.

8. A method of treating a disease in a mammal, comprising: administering to the mammal an effective amount of a composition comprising (i) a $C_n$-Ab, wherein $C_n$ is a fullerene or nanotube comprising n carbon atoms, and Ab is a moiety comprising an antigen-binding site and is covalently linked to the $C_n$, wherein the antigen-binding site recognizes an antigen associated with the disease, and (ii) a pharmaceutically-acceptable carrier.

9. The method of claim 8, the $C_n$ is substituted with one or more water-solubilizing groups.

10. The method of claim 8, wherein the Ab comprises an antigen-binding site selected from ZME-018, SCFVMEL, dSCFVMEL, GD2, HuM195, herceptin, BACH 250, ML 3-9, C 6.5, or αMMP9.

11. The method of claim 8, wherein the disease is an oxidative stress disease.

12. The method of claim 8, wherein the composition is administered at a dosage of from about 0.001 mg $C_n$ per kg body weight per day to about 1 g $C_n$ per kg body weight per day.

13. The method of claim 8, wherein the composition further comprises a therapeutic molecule associated with the $C_n$-Ab.

14. The method of claim 13, wherein the therapeutic molecule is paclitaxel, doxorubicin, vincristine, or cisplatin.

15. The method of claim 13, wherein the composition is administered at a dosage of from about 0.001 mg therapeutic molecule per kg body weight per day to about 1 g therapeutic molecule per kg body weight per day.

16. The method of claim 8, wherein the method further comprises administering an adjuvant to the mammal, wherein the adjuvant dissociates the therapeutic molecule from the $C_n$-Ab.

* * * * *